United States Patent
Keinath et al.

(12)

(10) Patent No.: US 6,610,487 B2
(45) Date of Patent: Aug. 26, 2003

(54) METHOD OF DIAGNOSING GUMMY STEM BLIGHT IN PLANTS USING A POLYMERASE CHAIN REACTION ASSAY

(75) Inventors: Anthony P. Keinath, Charleston, SC (US); Benesh M. Somai, Durban (ZA); Ralph A. Dean, Clemson, SC (US)

(73) Assignee: Clemson University, Clemson, SC (US)

( * ) Notice: Subject to any disclaimer, the term of this patent is extended or adjusted under 35 U.S.C. 154(b) by 82 days.

(21) Appl. No.: 09/758,073

(22) Filed: Jan. 10, 2001

(65) Prior Publication Data

US 2001/0024785 A1 Sep. 27, 2001

Related U.S. Application Data

(62) Division of application No. 09/255,432, filed on Feb. 22, 1999, now Pat. No. 6,258,537.
(60) Provisional application No. 60/078,103, filed on Mar. 16, 1998.

(51) Int. Cl.[7] .......................... C12Q 1/68; C01N 33/53; C07H 21/00; C07H 21/04
(52) U.S. Cl. .......................... 435/6; 435/91.2; 435/7.31; 435/7.92; 536/22.1; 536/24.3; 536/24.32; 536/25.32
(58) Field of Search .......................... 435/91.2, 6, 7.31, 435/7.92; 536/22.1, 24.3, 24.32, 25.32

(56) References Cited

U.S. PATENT DOCUMENTS 4,965,188 A    10/1990    Mullis et al.

OTHER PUBLICATIONS

A.P. Keinath, M.W. Farnham & T.A. Zitter: Morphological, Pathological, and Genetic Differentiation of *Didymella bryoniae* and *Phoma* spp. Isolated from Curcurbits; pp. 364–369; vol. 85, No. 3, 1995 Phytopathology.

W.R. Sitterly & A. P. Keinath; Gummy stem blight; pp. 27–28; 1996; Compendium of Cucurbit Diseases; T. A. Zitter, D. L. Hopkins, and C. E. Thomas, eds. APS Press, St. Paul, MN.

J. Gabriels, European Search Report Application No. EP 99 10 4751, 4 pages, Jan. 2, 2001, The Hague.

Keinath et al, "RAPD Fingerprinting and Phylogenetic Analysis of *Didymella bryoniae* and *Phoma* Species", Phytopathology, vol. 86, No. 11 Suppl., 1996, p. S35 (Abstract).

Keinath et al, "PCR Identification of Differentiation of *Didymella bryoniae* and *Phoma* Species", Phytopathology, vol. 87, No. 6 Suppl., 1997, p. S92 (Abstract).

Fujise O, Hamachi T, Hirofuji T, Maeda K Colorimetric microtiter plate based assay for detection and quantification of amplified *Actinobacillus actinomycetemcomitans* DNA, Oral Microbiol Immunol 1995: 10:372–377.

*Primary Examiner*—Gary Benzion
*Assistant Examiner*—Joyce Tung
(74) *Attorney, Agent, or Firm*—Dority & Manning, PA (57) ABSTRACT

The present invention provides a sensitive test for objectively diagnosing the presence of *Didymella bryoniae*, the causative agent of gummy stem blight, and differentiating it from similar, nonpathogenic Phoma species. The assay is applicable to DNA isolated from extracts from plant leaves, stem or seed. The detection method employs a polymerase chain reaction technique, using specific oligonucleotide primers for amplification. PCR Products can be visualized using an ELISA-based calorimetric detection system.

14 Claims, 4 Drawing Sheets

METHOD OF DIAGNOSING GUMMY STEM BLIGHT IN PLANTS USING A POLYMERASE CHAIN REACTION ASSAY

The present application is a divisional of application Ser. No. 09/255,432, filed Feb. 22, 1999, now U.S. Pat. No. 6,258,537, which claims the benefit of priority from a provisional application filed Mar. 16, 1998 and having U.S. Ser. No. 60/078,103.

FIELD OF THE INVENTION

The present invention is directed to the field of diagnostic tests for detecting the presence of the fungus responsible for causing gummy stem blight in plants and seeds. More specifically, the present invention provides a method by which *Didymella bryoniae*, the causative agent of gummy stem blight, may be objectively detected and differentiated from related non-pathogenic organisms using a rapid assay based on the polymerase chain reaction.

BACKGROUND OF THE INVENTION

Gummy stem blight, caused by infection with the fungal pathogen *Didymella bryoniae*, is a common disease affecting most cucurbits. Cucurbits refers to a botanical family, which includes among its members such agricultural crops as cucumbers, pumpkins, gourds, watermelons, cantaloupe, squash (summer and winter), and related plants. The fungus can infect both stems and leaves, in which case the disease is called gummy stem blight, or fruit, and is then referred to as black rot disease. The disease occurs worldwide and causes serious crop losses due to stem and fruit rot. In the United States, the pathogen is most common in the South, particularly the Southeastern regions where environmental conditions are ideal for the development and spread of the pathogen. In North Carolina, gummy stem blight is the second most important cucumber pathogen, and infection results in severe defoliation of plants in late production stages.

Traditional identification of fungal pathogens and subsequent diagnosis of plant diseases have usually involved growing the causative organism in pure culture, followed by characterization of the resultant colonies by examining spore morphology under a light microscope. However, such a diagnostic approach may be associated with technical problems. These include the inability to culture the disease-causing organisms, and the inaccuracy of diagnosis because closely related organisms may have similar morphological characteristics, making identification and differentiation between related species difficult. Further, the time required for culturing and differentiation of fungal pathogens ranges from 3 to 21 days. Thus, in addition to requiring a high degree of skill, such an approach to fungal identification may result in unacceptable time delays.

In the case of *D. bryoniae*, other problems exist which may make culture-based diagnosis difficult. For example, it has been reported that many *D. bryoniae* isolates fail to readily sporulate in culture and that those few that did sporulate seem to do so merely by chance. Therefore, traditional methods of identifying *D. bryoniae* may not always be successful, especially if sporulation is sporadic.

Additionally, several innocuous fungal species may be difficult to differentiate from *D. bryoniae*, thereby complicating diagnosis. For example, nonpathogenic Phoma species have also been isolated from tissues exhibiting gummy stem blight symptoms and are somewhat difficult to differentiate in the presence of *D. bryoniae*.

As an alternative to diagnosis based on culture and spore morphologies, a technique based on random amplified polymorphic DNA analysis (RAPDs) has been developed to identify and differentiate *D. bryoniae* from related Phoma species. This RAPD technique uses random primers to generate small fragments of DNA of the organism in question, using the polymerase chain reaction. These fragments are then electrophoresed and the resulting pattern or "fingerprint" compared to other isolates, to aid in classifying the test organism and identifying unique areas of DNA (see A. P. Keinath et al, 1995, Morphological, Pathological and Genetic Differentiation of *Didymella bryoniae* and Phoma spp. Isolated from Cucurbits, 85 *Phytopathology* 364). However, this assay requires many different random primers to generate the fingerprint. Owing to the short primer lengths, the assay requires low annealing temperatures, which may cause variation in banding pattern and result in inaccurate diagnosis.

Therefore, there is currently an urgent need for an accurate diagnostic test for the identification of the pathogen *D. bryoniae*, especially for use in infected greenhouse transplants where the disease can spread very rapidly. There is also a need for an assay which can easily and rapidly differentiate non-pathogenic fungal species from the gummy stem blight pathogen. Further, there is a need for an assay to diagnose *D. bryoniae* from plant material (including leaves, stems, and seed), as well as differentiate *D. bryoniae* infection from non-pathogenic organisms which may be present.

The Polymerase Chain Reaction (PCR) is a technique by which a small fragment of deoxyribonucleic acid (DNA) can be rapidly duplicated, or cloned, to produce multiple DNA copies. The strength of the PCR technique is that it can be used to identify organisms from minute amounts of tissue samples because it proceeds in a series of cycles, with each successive round doubling the amount of DNA present in the sample. Thus, more than one billion copies of a single DNA fragment can be made in just a few hours, by mimicking the natural DNA replication process that occurs in living cells.

There are three phases essentially in a PCR reaction. In the first phase, denaturation, the original DNA extracted from the sample is heated to a temperature of from about 90° C. to 95° C. for a brief period, causing the individual DNA strands to separate. In the second or annealing phase, the temperature of the sample tube is lowered over a short period of time, allowing for the added oligonucleotide primers to bind to the separated DNA strands in a complementary fashion. In the final polymerization phase, the temperature of the sample mixture is again raised, to approximately 72° C., allowing the polymerase enzyme to copy the DNA molecule rapidly. The three phases make up one complete PCR cycle, and take less than five minutes to complete.

The PCR reaction is repeated for a specified number of cycles, usually between 25 and 35, allowing the entire procedure to be completed in three to four hours. As an added advantage, this procedure can be automated with the use of commercially available thermal cyclers, allowing the entire procedure to be conducted using pre-determined parameters.

Following the completion of the PCR procedure, the samples may be run out on an electrophoresis gel to verify the presence of the desired DNA band. The electrophoresed products may be visualized using an ethidium bromide dye, or may be positively identified by hybridization with a probe specific for the bands of interest.

Over the past several years PCR technology has been shown to be applicable to the diagnosis of many human, animal, and plant organisms, and a variety of clinical assays have been evaluated. Results suggest that PCR is highly sensitive and, by varying conditions used, the technique can accurately discriminate between even closely related species.

PCR technology has never been used for diagnostic applications as in the present invention, because genetic sequences unique to *D. bryoniae* for use as primers have not been known. Nor have the primers and conditions suitable for differentiating closely related Phoma species from *D. bryoniae* been known.

By identifying specific primers unique to *D. bryoniae* and related Phoma sp., PCR technology can be used to provide an objective assay which overcomes some of the deficiencies of prior diagnostic methods for the identification and differentiation of *D. bryoniae*. Thus, the present invention allows for rapid diagnosis of gummy stem blight and requires only small amounts of fungal DNA infecting plant tissue or seed to provide a result.

SUMMARY OF THE INVENTION

The present invention recognizes and addresses the foregoing disadvantages and others of prior art constructions and methods.

Accordingly, it is an object of the present invention to provide a diagnostic assay for diagnosing gummy stem blight disease in plants.

Another object of the present invention is to provide a diagnostic test for gummy stem blight disease that is highly sensitive and rapid.

Yet another object of the present invention is to provide specific oligonucleotide primers which can be used to identify *D. bryoniae* DNA and differentiate it from closely related, non-pathogenic Phoma sp. DNA.

Still another object of the present invention is to provide a calorimetric assay for diagnosing gummy stem blight disease in plants.

It is still a further object of the present invention to provide a rapid diagnostic assay for determining the presence of *Didymella bryoniae* in plant tissues and seed.

It is yet another object of the present invention to provide a diagnostic test for differentiating the pathogenic fungus *Didymella bryoniae* from related, non-pathogenic Phoma species infecting plant tissues and seed.

These and other objects of the present invention are achieved by providing specific oligonucleotide primers in a PCR based assay to diagnose gummy stem blight in plants and differentiate the causative organism, *D. bryoniae*, from co-infecting nonpathogens.

The detection method utilizes the polymerase chain reaction, whereby DNA is extracted from potentially infected plant cells and is then replicated a number of times such that the original amount of DNA present is amplified greatly. The diagnostic assay requires the addition of unique primers, specific for *D. bryoniae* and for any organism desired to be differentiated from *D. bryoniae*, into a PCR reaction, thus resulting in enhanced amplification of a PCR product which can be putatively identified by visualization or definitively identified by hybridization with a specific probe.

For example, to identify the PCR product as *D. bryoniae*, a short oligonucleotide segment unique to *D. bryoniae* may be reacted with the PCR product and, if specific binding occurs, the PCR product is identified as *D. bryoniae*. Further, by reacting the product with probes for other organisms, the infective agent may be differentiated from co-infecting species, based on a negative hybridization result.

The PCR process is initiated by isolating genomic DNA from potentially-infected plants to serve as a template during the PCR amplification. Specific oligonucleotide primers are allowed to hybridize, or bind, to areas which are complementary in the target DNA. The primers then serve as sites to allow the polymerase enzyme to fill in the area between the bound primers, resulting in a doubling of the DNA. By repeating this cycle many times, a billion or more copies of the original DNA can be made. Specificity of the amplification procedure is controlled by the uniqueness of the primers, and the conditions of the PCR reaction.

Following PCR amplification, PCR products are electrophoresed into agarose gels, along with a DNA ladder for determining the size of the PCR product. The PCR product can be putatively identified using visual comparison to a size marker, or can be definitively identified by means of hybridization with a specific probe.

The present diagnostic method will allow for early detection and differentiation of fungal lesions on the leaves and stems of plants, or infection of seeds. Because PCR technology can amplify very small quantities of fungal DNA, the presence of *D. bryoniae* or other organisms can be detected in amounts so small that no visible sign of infection is present. Such early detection allows for rapid implementation of control measures, such as fungicide spraying in production fields, and permits identification of infected seed before marketing.

As discussed above, the present invention consists of a method for detecting *D. bryoniae*, and for differentiating this pathogenic organism from closely related non-pathogenic Phoma species, by detecting a unique segment of fungal DNA in plant tissues and seeds. The present method is more rapid, and may be more sensitive, than identifying *D. bryoniae* in pure culture and examining spore morphology under the light microscope. Further, the present method is less time consuming and labor intensive than using RAPD fingerprint analysis to differentiate between *D. bryoniae* and other Phoma species, since many different random primers have to be used to verify the accuracy of the results obtained with the RAPD technology.

The present method is also more cost effective when compared with currently used methods. Culture methods may require large amounts of special media and a high degree of skill to differentiate morphological characteristics of cultured organisms. Further, co-infecting organisms may not grow in the media chosen, resulting in inaccurate results. In contrast, the present diagnostic assay permits the simultaneous amplification of multiple samples and can be accomplished using very small amounts of fungal DNA, on the order of 50 nanograms (ng) or less.

Broadly speaking, the diagnostic method involves extracting genomic DNA from cells found in plant tissue, such as stems and leaves, or seed; replicating the DNA template with the use of specific oligonucleotide primers; amplifying the complimentary DNA for approximately 30 cycles of thermal cycling; and producing the PCR products which can be identified based on size or on hybridization ability with an oligonucleotide probe specific for D. bryoniae or other fungal species.

In summary, the present method of detecting gummy stem blight, using unique oligonucleotide primers to amplify a *D. bryoniae* sequence and differentiating *D. bryoniae* from closely related, non-pathogenic Phoma species, could greatly increase early treatment and control of gummy stem blight in greenhouses, commercial production fields, and seed production fields.

BRIEF DESCRIPTIONS OF THE FIGURES

The file of this patent contains at least one drawing executed in color. Copies of this patent with color drawing(s) will be provided by the Patent and Trademark Office upon request and payment of the necessary fee.

A full and enabling disclosure of the present invention, including the best mode thereof, to one of ordinary skill in the art, is set forth more particularly in the remainder of the specification, including reference to the accompanying figures, wherein.

DETAILED DESCRIPTION OF PREFERRED EMBODIMENT

Other objects, features and aspects of the present invention are disclosed in, or are obvious from, the following Detailed Description. It is to be understood by one of ordinary skill in the art that the present discussion is a description of exemplary embodiments only and is not intended as limiting the broader aspects of the present inventions which broader aspects are embodied in the exemplary construction.

The detection method of the present invention utilizes the polymerase chain reaction (PCR) technique, whereby total genomic DNA is extracted from potentially infected plant tissues, cells, and seed, and the fungal DNA is then amplified using specific oligonucleotide primers to target desired DNA regions for replication and amplification. If the DNA sequence complimentary to the oligonucleotide primers is found in the samples to be analyzed, a PCR product will be generated that can be visualized using non-specific methods, like ethidium bromide staining, or specific methods, like hybridization with unique oligonucleotide probes to definitively identify the PCR product.

The present diagnostic method involves isolating genomic DNA from cells of plant leaves, stems, or seed, using techniques well known to those skilled in the art. Standard molecular biology textbooks, such as METHODS FOR GENERAL AND MOLECULAR BACTERIOLOGY, eds., Philipp Gerhardt, et al, American Society for Microbiology, Washington, D.C., 1994, may be consulted for procedures to isolate DNA, without undue experimentation.

Initially during the PCR process, the sample DNA is denatured such that the double stranded DNA is separated into individual strands. Each strand is then replicated, using a pair of specific oligonucleotide primers that give rise to a PCR product of particular size. For example, the D. bryoniae primer pair (DB) gives rise to a product approximately 650 base pairs (bp) in length, as does the Phoma medicaginis-like primer pair (PM), while a 450 bp fragment results from amplification with the D. bryoniae—NY variant primer pair (NY).

In a preferred embodiment, the sample DNA is amplified using the PCR technique for about 30 cycles; then the resulting product is electrophoresed onto agarose gels for verification. In one embodiment, the PCR product is visualized by incorporating ethidium bromide, a dye which exhibits strong affinity for DNA, into the agarose gel. The PCR product is then visualized under ultraviolet light and its size estimated by comparison with a known standard, like a Lambda DNA marker.

In another preferred embodiment, template DNA is amplified with modified PCR primers specific for a particular group of organisms. Modification of the primers involves the addition of a biotin moiety to the 5' end of the forward primer and the addition of a fluorescein moiety to the 5' end of the reverse primer. Amplification of genomic DNA is then performed for approximately 30 cycles. Visualization of the PCR products is performed using a calorimetric method. The amplified DNA is first attached to the wells of a microtiter plate coated with avidin (NEUTRAVIDIN), which binds the DNA chemically via the biotin moiety. After washing off excess or unbound PCR product, an enzyme is attached to the DNA via the fluorescein moiety. Excess or unbound enzyme is washed away prior to the addition of a color substrate. The enzyme reacts with the substrate forming a colored product. The intensity of the color can be measured using commercially available readers (ELISA readers), thus permitting the rapid processing of multiple samples.

Specifically, the diagnostic method involves the following steps:

(a) removing a sample of leaf, stem, or seed to be tested for gummy stem blight from the plant; (b) extracting the DNA from the cells of the sample to use as a template; (c) replicating the desired region in the DNA template by binding specific oligonucleotide primers in a complementary fashion, such primers designed to give rise to a PCR product having a size different from the size of a product produced from amplifying any undesired genomic DNA; (d) amplifying complimentary DNA by conducting the polymerase chain reaction for about 30 cycles; and (e) identifying the PCR product by agarose gel or ELISA visualization or probe hybridization to determine whether a sequence unique to D. bryoniae, or to closely related Phoma species, is present.

The present invention may be better understood by reference to the following examples:

EXAMPLE 1

Cultivation of Fungal Isolates

*D. bryoniae* and Phoma sp. isolates were obtained from several sources. The South Carolina (SC) isolates were originally isolated from commercial cucumber, cantaloupe and watermelon fields and were obtained in pure culture from A. P. Keinath. A second set of fungal isolates was obtained in pure culture from T. A. Zitter and originated from various regions within the United States (NY, AZ, WI, FL, and NC). Other isolates were furnished by a seed company for testing, while a fourth set was obtained from infected material (leaves, stem or fruit tissue) from commercial fields. The geographical origins of the isolates are as follows:

| ISOLATE CLASSIFICATION | ORIGIN | HOST | DESIGNATION |
|---|---|---|---|
| New York (NY) | Florida | muskmelon | FL1 |
| | Florida | watermelon | FL2 |
| | Arizona | muskmelon | AZ1 |
| | Wisconsin | muskmelon | Wis1 |
| | N. Carolina | cucumber | NC1, NC2 |
| | New York | muskmelon | NY1, NY2, NY3, NY5, NY13, NY14, NY20, NY21 |
| | New York | watermelon | NY4 |
| | New York | cucumber | NY6, NY10, NY11, NY19 |
| | New York | pumpkin | NY7, NY12, NY17 |
| | New York | butternut squash | NY8, NY9, NY15, NY16, NY18 |
| South Carolina | Edisto, SC | cantaloupe | C45, C46, C48, C49, C51, C53, C55, C76, C79, C81, C82 |
| | Edisto, SC | cucumber | C61, C62, C63, C64, C65, C66, C67, C68, C69, C70, C72, C73, C74, C75 |
| | Edisto, SC | watermelon | W73, W74, W95, W97, W99, W100, W101, W103 |
| GSB 95 | Colleton, SC | watermelon | A1, A2, A3, A4, A5, A8, A9, A11, B1, B2, B3, B4, B5, B6, B7, B8, B9, B10 |
| | Colleton, SC | cantaloupe | D1, D2, D3, D4, C5, C6, D7, C8, D9, D10, D11, D12, D13, D14, D15, D16, D17, D18, D19, D20 |
| | Edisto, SC | cantaloupe | F1, F2, F3, F4, F5, F6, F7, F8, F9, F10, F11, F12, F14, F15, F16, F17, F18, F10, F20 |
| | Edisto, SC | watermelon | G1, G2, G3, G4, G5, G6, G7, G8, G9, G12, G13, G14, G15, G16, G17, G18, G19, G20 |
| | Chesterfield,SC | cantaloupe | J1, J2, J3, J4, J5, J6, J7, J8, J9, J10, J12, J15, J16, J17, J20, J21, J23, J24 |
| | Chesterfield, SC | watermelon | K3, K8, K10, K12, K15, K16, K17, K20 |
| "Blind" test samples | Unknown | Unknown | W200, W201, W202, W203, W204, W205, W206, W207, W208, W209 |

The *D. bryoniae* and Phoma sp. isolates were grown on one-quarter strength potato-dextrose agar (QPDA) at ambient temperatures (22–24° C.) for a 12-hour photoperiod for 2 weeks or until pycnidia were produced.

Preliminary identification was accomplished based on spore morphology characteristics.

EXAMPLE 2

Genomic DNA Isolation

*D. bryoniae*, Phoma sp. isolates, and those isolates identified as unknown were grown as described in Example 1, on QPDA in the dark for three days at ambient temperature. Cultures were flooded with 5 ml of sterile distilled water and scraped to remove mycelium, which was used to seed liquid cultures. Fungi were grown in sucrose-casein-salts liquid medium, 50 ml per 250-ml flask, for 2–3 days at ambient temperature in the dark. Cultures were decanted through four layers of sterile cheesecloth, and mycelium was washed with sterile distilled water. After removing as much liquid as possible, mycelium was frozen and stored at −20° C.

Genomic DNA was extracted as follows: 1.0 g of mycelium was harvested in eppendorf tubes and snap-frozen in liquid nitrogen before storing at −80° C. until use. Frozen mycelium was ground to a fine powder using a mortar and pestle, and mixed with 5 ml of lysis buffer (50 mM TRIS-HCl, pH 7.5; 50 mM EDTA, pH 8.0; 3% sodium dodecyl sulphate [SDS]; and 1% 2-Mercaptoethanol) to a smooth consistency and incubated at 65° C. for one hour. The suspension was extracted twice with equal volumes of phenol:chloroform:isoamyl alcohol (25:24:1), once with chloroform:isoamyl alcohol (24:1), and precipitated at room temperature with 0.1 volume of 3 M sodium acetate and 1.5 volume of cold isopropanol. The precipitate was spooled with a hooked glass rod, washed with 70% ethanol and resolublized in water. The DNA concentration was determined with a fluorometer (Hoefer TKO 100) and adjusted to 10 ng/μl.

For restriction digests, DNA was further treated with 100 μg/ml proteinase K at 56° C. for one hour; RNase-treated (100 μg/ml) at 37° C. for one hour; phenol:chloroform extracted; precipitated as above and resolubilized in TE buffer (10 mM TRIS-HCl; 1 mM EDTA).

DNA from 1 g of cucumber, cantaloupe, watermelon, squash and pumpkin leaves was independently isolated in an identical fashion as for fungal DNA except that after the addition of lysis buffer, the suspension was incubated at 65° C. for two hours before phenol:chloroform extraction. The final pellet was resuspended in water prior to use.

EXAMPLE 3

Identification of *D. Bryoniae* and Phoma-Species Specific Primers

PCR-based RAPD analysis was completed as described by A. P. Keinath, M. W. Farnham, and T. A. Zitter, in Morphological, Pathological and Genetic Differentiation of *Didymella bryoniae* and *Phoma* sp. Isolated from Cucurbits, 85 *Phytopathology* 364 (1995), as follows:

Commercial RAPD 10-mer oligonucleotide primers were purchased from Operon Technologies (Alameda, Calif.) and used to prime PCR. Ten Operon primers were chosen to evaluate all fungal isolates as follows: T1 (SEQ ID:1): GGGCCACTCA; T7 (SEQ ID:2): GGCAGGCTGT; T12 (SEQ ID:3): GGGTGTGTAG; T13 (SEQ ID:4): AGGACT- GCCA; T14 (SEQ ID:5): AATGCCGCAG; T18 (SEQ ID:6) :GATGCCAGAC; K1 (SEQ ID:7): CATTCGAGCC; K4 (SEQ ID:8): CCGCCCAAAC; K8 (SEQ ID:9): GAA- CACTGGG; and K9 (SEQ ID:10): CCCTACCGAC.

The PCR reaction mixture contained 40 ng of genomic DNA, 2.5 µl of 10X buffer, 1.9 mM $MgCl_2$, 25 µg of nonacetylated bovine serum albumin (New England Biolabs, Beverly, Mass.), 0.1 mM deoxynucleotide triphosphates, 0.32 µM primer, and 1.5 units of Taq DNA polymerase (Promega Corp, Madison, Wis.) in a total volume of 25 µl. Final PCR reaction volumes were brought up to 25 µl with sterile water. All tubes were overlaid with one drop of mineral oil, and PCR amplification was performed in a Perkin-Elmer-Cetus (Norwalk, Conn.) Thermal Cycler 480, as follows:

Reaction conditions were initial denaturation at 94° C. for 2 min, followed by 45 cycles of denaturation at 94° C. for 1 min, annealing at 36° C. for 1 min and extension at 72° C. for 2 min. A final extension at 72° C. for 3 min was done before holding samples at 4° C. until use. The entire 25 µl sample volume was loaded into a 1.5% agarose gel for electrophoresis at 6V/cm with 1X TAE buffer (40 mM Tris; 20 mM Glacial acetic acid; 1 mM EDTA). Products were visualized by staining gels with ethidium bromide at 0.5 µg/ml.

RAPD PCR was repeated at least once for several of the primers to evaluate reproducibility. To identify unique PCR fragments, RAPD profiles of one representative isolate from each population group were generated, separated on 1.5% agarose gel and blotted onto Nylon membranes (Amersham, Arlington Heights, Ill.) by overnight capillary transfer. Purified, sheared genomic DNA of one of the *D. bryoniae* isolates was labeled with $P^{32}$-dCTP by random-primed labeling (Multiprime DNA Labeling System, Amersham, Arlington Heights, Ill.) and hybridized to the membrane-bound RAPD DNA bands at 65° C. overnight. Filters were washed in 1X SSC (150 mM NaCl; 15 mM sodium citrate) and 0.1% SDS at 65° C. for 20 min. Membranes were exposed to X-O-MAT autoradiography film (Kodak, VWR Scientific, Suwanee, Ga.) at −80° C. with intensifying screens.

After appropriate exposure, membranes were stripped, and individually re-probed with labeled genomic DNA from one of the isolates of the Phoma group. This allowed an average of two to three putatively unique non-hybridizing bands from the Phoma group to be identified when DNA from *D. bryoniae* was used as a probe and visa versa.

For each primer used, a visual comparison was made between profiles for all isolates. Evaluation of RAPD hybridization fingerprints allowed an average of two to three putatively unique fragments per RAPD primer to be identified. However, many false positive bands were obtained. By screening 40 RAPD primers, only two unique RAPD fragments each were positively identified for the three groups consisting of *D. bryoniae*, *D. bryoniae*-New York variant and *P. medicaginis*-like isolates.

It is estimated that there was greater than 90% cross-hybridization between *D. bryoniae* and *D. bryoniae*-New York variant isolates. By contrast, *D. bryoniae* and *D. bryoniae*-New York variant isolates exhibited only about 5% cross-hybridization with *P. medicaginis*-like isolates, based on RAPD hybridization fingerprint analysis.

Non-hybridizing RAPD fragments were excised from the agarose gels and the DNA isolated by freeze squeeze. This DNA was ligated overnight at 4° C. into the pGEM® T-EASY (Promega) PCR cloning vector plasmid. Ligated DNA was electroporated into electrocompetent BG33R *E. coli* cells and colonies screened using the X-gal blue/white screening procedure on Luria-Bertani (LB)/ampicillin plates. Plasmid DNA was purified using the WIZARD® PLUS (Promega) plasmid DNA purification system. DNA inserts were released by restriction with EcoR I, separated by gel electrophoresis, blotted onto Nylon membranes and probed with the appropriate RAPD DNA fragment to identify positive clones.

Cloned inserts were sequenced both in the forward and reverse directions using an ABI florescent dye-terminator cycle sequencing ready reaction kit (Perkin-Elmer, Foster City, Calif.) according to the manufacturer's instructions. Sequences were subjected to polyacrylamide gel electrophoresis and read on the ABI 373 automatic sequencer.

Based on sequence information, 21-mer primers with a GC content of about 50% were designed for amplification of as large a PCR fragment as possible. Primers were synthesized and purified by Integrated DNA Technologies (Coralville, Iowa).

Primer sequences are as follows:

*Didymella bryoniae* (DB) Primer Set:

(SEQ ID:11)
(i) Forward primer: TGT CGT TGA CAT CAT TCC AGC (SEQ ID:12)
(ii) Reverse primer: ACC ACT CTG CTT AGT ATC TGC

*Phoma medicaginis*-like (PM) Primer Set:

(SEQ ID:13)
(i) Forward primer: GTC AGA GTT CAG AAT GCT TCG (SEQ ID:14)
(ii) Reverse primer: ACG GAT GAA TAA CAC GGA AGA

*Didymella bryoniae*-New York variant (NY) Primer Set:

(SEQ ID:15)
(i) Forward primer: GCT AAG CCT TAA TCT AGC TGC (SEQ ID:16)
(ii) Reverse primer: GAG AGT AAG CTA ACC TAA AGG

EXAMPLE 4

PCR Identification of Fungal Isolates

DNA was extracted from various fungal isolates as indicated in Example 2, and used as a template for the PCR-based diagnostic assay. The PCR reaction was carried out as described in Example 3, except that all reaction volumes contained 40 ng of fungal DNA as template, 10 ng of forward and reverse DB primers, and 40 ng of both PM and NY primer sets.

Final PCR reaction volumes were brought up to 25 µl with sterile water and tubes were overlaid with two drops of mineral oil. Thermal cycling conditions were an initial denaturation at 94° C. for 1 min, followed by 30 cycles of denaturation at 94° C. for 1 min, annealing at 64° C. for 1 min. and extension at 72° C. for 2 min. At the end of 30 cycles, a final extension at 72° C. for 10 min. was performed and samples were held at 4° C. until use.

10 µl of each sample was mixed with small fragment loading dye (0.1% xylene cyanol; 50% glycerol), loaded into 1% agarose gels containing ethidium bromide and subjected to electrophoresis at 5V/cm in 1X TAE buffer for 1 hour. Gels were photographed using black and white Polaroid film.

Results have been compiled for more than 145 isolates according to the method of the present invention. All but ten of these isolates have also been cultured and identified based upon morphologic criteria and, in all cases, the morphological classification confirmed results obtained with the PCR identification method.

The isolates tested were classified as follows:

NY10, NY11, NY12, NY13, NY14, NY15, NY16, NY17, blank (remaining wells are empty).

Figure 1:
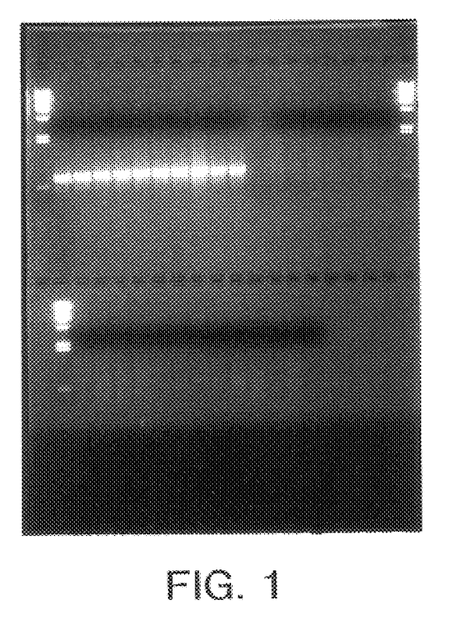
FIG. 1 is a photograph showing the agarose gel results from PCR identification of fungal isolates, using the DB primer set.

As can be seen in FIG. 1, the DB primer set identified samples 2–11 as *D. bryoniae* isolates, as indicated by the appearance of a band of desired size in the lane. None of the other samples were amplified by the DB primer set, indicating that these isolates were not *D. bryoniae*.

Figure 2:
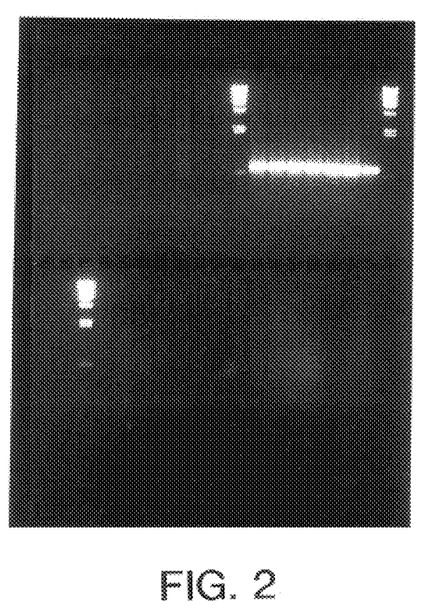
FIG. 2 is a photograph showing the agarose gel results from PCR identification of fungal isolates, using the PM primer set.

In FIG. 2, results demonstrate that lanes 12 through 18 are from samples identified as *P. medicaginis*-like isolates. Again, no PCR products are present in the remaining samples, showing that the PM primer set is also highly specific to *P. medicaginis*-like isolates.

Figure 3:
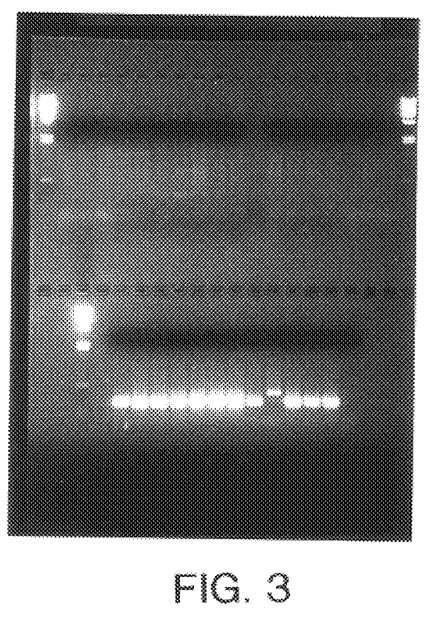
FIG. 3 is a photograph showing the agarose gel results from PCR identification of fungal isolates, using the NY primer set.

FIG. 3 shows the results of amplification of the samples using the NY primer set. A band is visible only in the lanes which contain *D. bryoniae*-New York variant isolates. However, in lane 13 on the bottom row of the gel (sample NY14), a larger band than expected was amplified, indicating that this isolate is not a *D. bryoniae*-New York variant organism. The identity of this isolate is still unknown.

| CLASSIFICATION | ISOLATE DESIGNATION |
| --- | --- |
| *D. bryoniae* | FL1, FL2, Wis1, NY1, NY2, NY3, NY4, NY5, NY6, C61, C62, C64, C66, C68, C69, C70, C72, C74, C45, C46, C48, C49, C51, C53, C76, C79, C81, C82, W73, W74, W95, W99, W100, W101, W103, A4, A5, A8, A9, A11, B4, B5, B6, B7, B8, B9, B10, D1, D2, D3, D4, D5, D6, D7, D8, D9, D10, D11, D12, D13, D14, D15, D16, D17, D18, D19, D20, F1, F3, F4, F5, F6, F7, F8, F9, F10, F11, F12, F14, F15, F16, F17, F18, F19, F20, G1, G2, G3, G4, G5, G6, G7, G8, G9, G12, G13, G14, G15, G16, G17, G18, G19, G20, J1, J2, J3, J4, J5, J6, J7, J8, J9, J10, J12, J15, J16, J17, J20, J21, J23, J24, K3, K8, K10, K12, K15, K16, K17, K20, W200, W205, W206, W207, W208 |
| *P. medicaginis*-like | NC1, NC2, NY18, NY19, NY20, NY21, C63, C65, C67, C73, C75, C55, W97, A1, A2, A3, B1, B2, B3, F2, W202 |
| *D. bryoniae*-New York variant | AZ1, NY7, NY8, NY9, NY10, NY11, NY12, NY13, NY14, NY15, NY16, NY17, W201 |
| Unknown | W203, W204, W209 |

FIGS. 1, 2, and 3 are photographs of agarose gel results from representative experiments. The gels in these photographs show the PCR products resulting from amplification of the various isolates using the DB primers, PM primers, and NY primer sets respectively.

The gel in FIG. 1 was loaded as follows:
Top Row of Gel: Lambda DNA marker, FL1, FL2, Wis1, NY1, NY2, NY3, NY4, NY5, NY6, W95, empty, NC1, NC2, W97, NY18, NY19, NY20, NY21, Lambda DNA marker.
Bottom Row of Gel: Empty, Lambda DNA marker, Az1, NY7, NY8, NY9, NY10, NY11, NY12, NY13, NY14, NY15, NY16, NY17, blank (remaining wells are empty).

The gel in FIG. 2 was loaded as follows:
Top Row of Gel: FL1, FL2, Wis1, NY1, NY2, NY3, NY4, NY5, NY6, W95, Lambda DNA marker, NC1, NC2, W97, NY18, NY19, NY20, NY21, Lambda DNA marker, empty lane.
Bottom Row of Gel: Empty lane, empty lane, Lambda DNA marker, AZ1, NY7, NY8, NY9, NY10, NY11, NY12, NY13, NY14, NY15, NY16, NY17, blank (remaining wells are empty).

The gel in FIG. 3 was loaded as follows:
Top Row of Gel: Lambda DNA marker, FL1, FL2, Wis1, NY1, NY2, NY3, NY4, NY5, NY6, W95, empty lane, NC1, NC2, W97, NY18, NY19, NY20, NY21, Lambda DNA marker.
Bottom Row of Gel: Empty lane, empty lane, Lambda DNA marker, empty lane, Az1, NY7, NY8, NY9,

EXAMPLE 5

Elisa Detection of PCR Products

In a preferred embodiment, PCR products were visualized using a calorimetric method; a method which is easily adapted to automatic measurement using an ELISA reader. *D. bryoniae*, *P. medicaginis*-like, and *D. bryoniae*-New York variant primer sets were synthesized as in Example 3, except that a biotin and a fluorescein label were incorporated into the 5' end of the forward and reverse primers respectively. After amplification, PCR products were immobilized onto an avidin-coated microtiter plate (NEUTRAVIDIN, Pierce, Rockford, Ill). Prior to adding DNA, the NEUTRAVIDIN microtiter plates were washed two times with 200 µl phosphate buffered saline plus Tween 20 (PBS/T=1 L PBS +5 ml Tween-20). After the second wash, the plates were blotted dry to remove remaining liquid from the wells.

Into each well, 10 µl of Tris-EDTA (TE) and 10 µl of DNA from the PCR products was added, mixed by repeated pipetting, and incubated for 30 min at room temperature.

Following incubation, the DNA was removed and the wells washed 4X with PBS/T. The plates were allowed to stand for 3 min between washes. After the third wash, the plates were blotted dry and 100 pl of diluted enzyme conjugate (Chemicon, Temecula, Calif.)(1:2000 dilution) in phosphate buffer, pH 7.0, supplemented with between 0.1 mg/ml to 2.0 mg/ml bovine serum albumin) was added. The enzyme conjugate used was horseradish peroxidaseconjugated anti-fluorescein antibody. Following addition of the antibody, the plates were incubated for a further 30 min at room temperature. Excess antibody was removed by washing the wells 4X with PBS/T, and then 100 µl of diluted substrate was pipetted in each well. The substrates used were:

tetramethylbenzidine (TMB), supplemented with 0.5 µl of 1% hydrogen peroxide/ml of substrate, for detecting *D. bryoniae*, O-Phenylenediamine (OPD), supplemented with 0.4 µl of 30% hydrogen peroxide/ml of substrate, for detecting *P. medicaginis*-like isolates, and Azino-bis-ethylbenzthiazoline sulfonic acid (ABTS), supplemented with 0.5 µl of 30% hydrogen peroxide/ml of substrate, for detecting *D. bryoniae*-New York variant isolates.

After each substrate was added, the plates were incubated for 15 min in the dark at room temperature. The reactions were then stopped either with 10 µl of SDS (TMB and ABTS) or 3M sulfuric acid (OPD). Contents of each well were mixed by repeated pipetting, and color absorbance values were read in an ELISA reader. TMB and ABTS plates were read at a wavelength of 405 nm, while OPD plates were read at 490 nm.

Figure 1A:
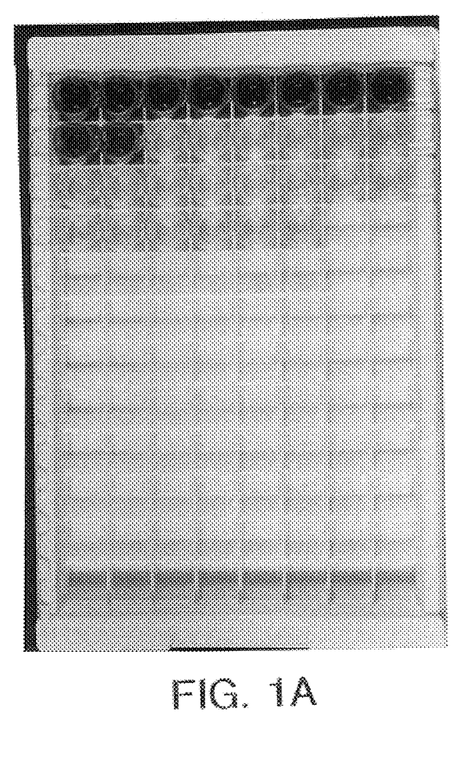
FIG. 1A is a photograph showing the microtiter plate containing the PCR products resulting from PCR amplification using the DB primer set, visualized using the TMB substrate in the ELISA calorimetric assay.
Figure 2A:
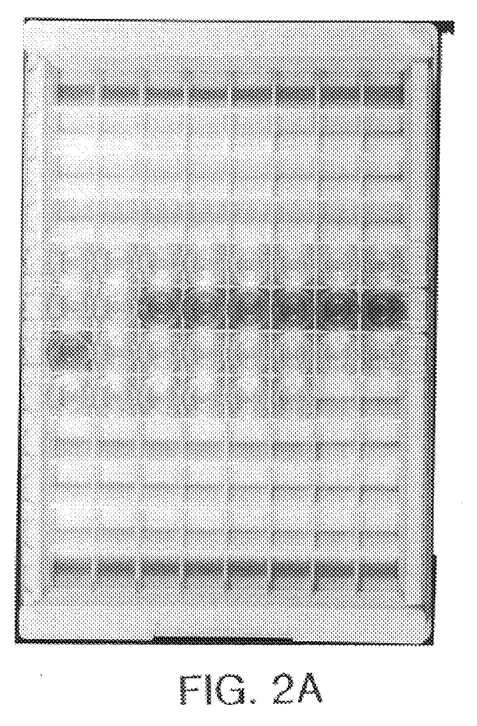
FIG. 2A is a photograph showing the microtiter plate containing the PCR products resulting from PCR amplification using the PM primer set, visualized using the OPD substrate in the ELISA calorimetric assay.
Figure 3A:
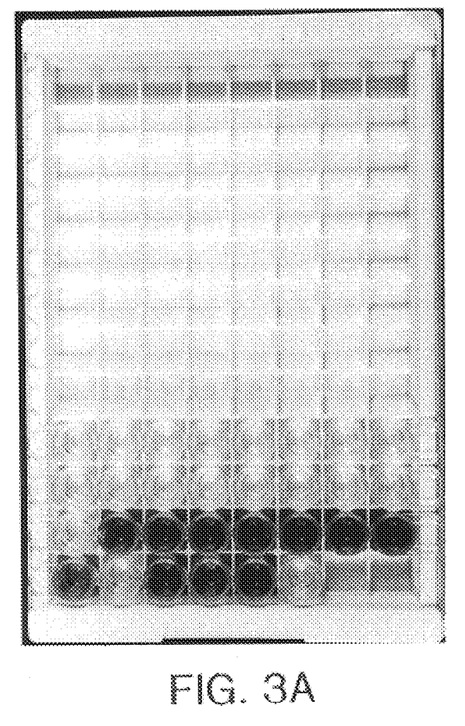
FIG. 3A is a photograph showing the microtiter plate containing the PCR products resulting from PCR amplification using the NY primer set, visualized using the ABTS substrate in the ELISA calorimetric assay.

FIGS. 1A, 2A, and 3A are photographs of microtiter plates containing the PCR products, produced by the PCR Assay in Example 4, and visualized using the ELISA calorimetric method described above.

The plates in FIGS. 1A, 2A and 3A are labeled across the top (columns) as 1–8, and from top to bottom (rows) as A to L.

The plate in FIG. 1A was loaded as follows: A1=Fl1, A2=F12, A3=Wis1, A4=NY1, A5=NY2, A6=NY3, A7=NY4, A8=NY5, B1-NY6, B2=W95, B3=NC1, B4=NC2, B5=W97, B6=NY18, B7=NY19, B8=NY20, C1=NY21, C2=Az1, C3=NY7, C4=NY8, C5=NY9, C6=NY10, C7=NY11, C8=NY12, Dl=NY13, D2=NY14, D3=NY15, D4=NY16, D5=NY17, D6=blank.

The blue color in wells A1–A8 and B1–B2 represent a positive test for the presence of PCR products amplified with the DB specific primers, thus indicating that those samples were amplified from *D. bryoniae* isolates.

The plate in FIG. 2A was loaded into the wells from rows E to H, as follows: E1=Fl1, E2=F12, E3=Wis1, E4=NY1, E5=NY2, E6=NY3, E7=NY4, E8=NY5, F1=NY6, F2=W95, F3=NC1, F4=NC2, F5=W97, F6=NY18, F7=NY19, F8=NY20, G1=NY21, G2=AZ1, G3=NY7, G4=NY8, G5=NY9, G6=NY10, G7=NY11, G8=NY12, H1=NY13, H2=NY14, H3=NY15, H4=NY16, H5=NY17, H6=blank.

In FIG. 2A, the positive wells are colored orange as a result of the OPD substrate used to detect the *P. medicaginis*-like PCR products. Results show that the PCR products in wells F3–F8 and G1 positively originated from *P. medicaginis*-like isolates by the PCR Diagnostic Assay.

The final photograph, 3A, was loaded into Rows I through L, as follows: I1=Fl1, I2=F12, I3=Wis1, I4=NY1, I5=NY2, I6=NY3, I7=NY4, I8=NY5, J1=NY6, J2=W95, J3=NC1, J4=NC2, J5=W97, J6=NY18, J7=NY19, J8=NY20, K1=NY21, K2=Az1, K3=NY7, K4=NY8, K5=NY9, K6=NY10, K7=NY11, K8=NY12, L1=NY13, L2=NY14, L3=NY15, L4=NY16, L5=NY17, L6=blank.

The green color in wells K2–K8, well L1, and wells L3–L5 represent a positive test for the presence of PCR products amplified with the NY specific primers, thus indicating those samples were amplified from *D. bryoniae*-New York variant isolates.

EXAMPLE 6

PCR Identification of Fungal Isolates Using Plant Lesion Extracts

Leaf Inoculation: Conidia from several *D. bryoniae* (WI1, FL2, C70, DBPum8, SSQ1), *P. medicaginis*-like (NY21, W97, NC1, DBPum11, NY18), and *D. bryoniae*-New York variant (AZ1, NY8, NY190, BY12, NY16) isolates were harvested from two-week-old fungal cultures as previously described in Example 1, and adjusted to a final concentration of $10^5$ conidia/50 µl. Cucumber (cv. Dasher), cantaloupe (cv. Classic), watermelon (cv. Jubilee II), pumpkin (cv. Howden) and butternut squash (cv. Waltham) were seeded in potting soil (METROMIX, Grace-Siera, Milpitas, Calif.) and grown in a growth chamber at 30° C. for about 10 days, until the cotyledons had fully expanded. The cotyledons were injured by pricking them several times with a sterile needle before inoculating 50 µl of conidia suspension onto the injured leaf regions. Each fungal isolate was inoculated back onto the host from which it was originally isolated. Plants were maintained at 100% relative humidity in a humidity chamber for 1 to 3 weeks to promote lesion development. When lesions reached a diameter of 10 to 20 mm, 5-mm leaf disks were excised from the lesion margins using a paper punch. All leaf disks were stored at –80° C. until used.

Isolation of Crude Lesion Extracts: For crude DNA isolation from leaf disks, one leaf disc was crushed in an Eppendorf tube with a screwdriver to a fine pulp in 40 µl, of TPS lysis buffer. To pellet leaf debris, the mixture was incubated at 65° C. for 20 min and centrifuged at high speed in a microcentrifuge for 5 min. The supernatant was removed, diluted 1:5 in sterile water, and stored at 4° C.

PCR Identification: For PCR detection of fungal DNA from crude lesion extracts, conditions were as outlined in Example 4, except that primer concentration for both the PM and NY primer sets was decreased to 20 ng and the annealing temperature was reduced to 61° C.

Figure 4:
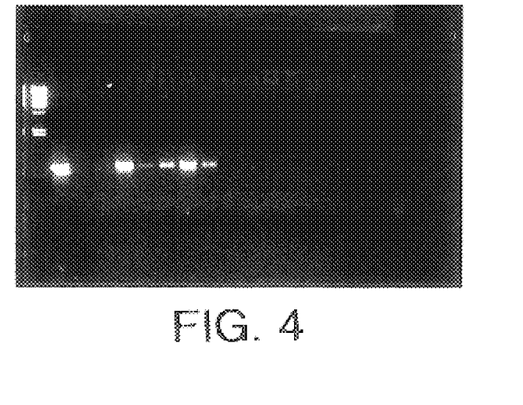
FIG. 4 is a photograph showing agarose gel results from PCR amplification of crude plant lesion extracts using the DB primer set.
Figure 5:
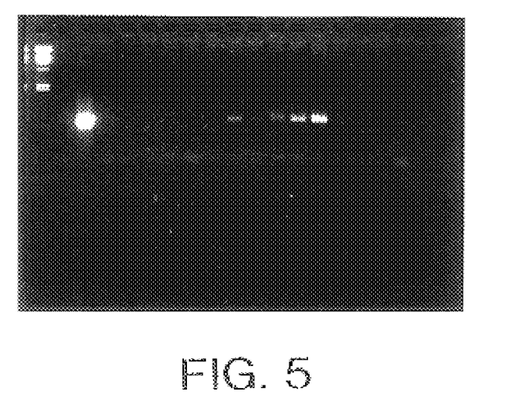
FIG. 5 is a photograph showing the agarose gel results from PCR amplification of crude plant lesion extracts using the PM primer set.
Figure 6:
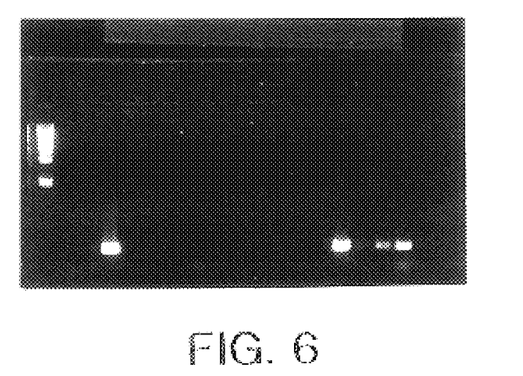
FIG. 6 is a photograph showing agarose gel results from PCR amplification of crude plant lesion extracts using the NY primer set.

FIGS. 4, 5 and 6 are photographs of agarose gel results from PCR amplification of fungal DNA isolated using plant lesion extracts. Lanes 1, 2 and 3: *D. bryoniae* FL2, *P. medicaginis*-like NY21, and *D. bryoniae*-New York variant AZ1 pure DNA controls. Lanes 4–8: DNA from *D. bryoniae* lesions; Lanes 9–13: DNA from *P. medicaginis*-like lesions; and Lanes 14–18: DNA from lesions caused by *D. bryoniae*-New York variant isolate. Lane 19 is a blank. Isolates in all gels are identical except that amplification in FIG. 4 was performed with the DB primer set; in FIG. 5 with the PM primer set; and in FIG. 6 with the NY primer set.

Results of this experiment show the primer sets successfully amplify crude fungal DNA extracts isolated from lesion extracts from inoculated seedlings. All extracts from *D. bryoniae* and *P. medicaginis*-like lesions yielded the 650 bp PCR product, while extracts from the lesions caused by *D. bryoniae*-New York variant isolates yielded the 450 bp fragment only when amplified with the appropriate primer set. The DB primers did not amplify extracts from either *P. medicaginis*-like or *D. bryoniae*-New York variant lesions and vice versa. Similarly, the *P. medicaginis*-like primers did not amplify extracts from *D. bryoniae*-New York variant lesions and vice versa. For many of the isolates from the *P. medicaginis*-like and groups, no detectable lesions had formed on injured, inoculated leaves, yet PCR analysis indicated the presence of fungal DNA from these groups.

The results presented in Example 6 also demonstrate that the isolation buffer used successfully neutralized both plant and fungal inhibitors, such as phenolic compounds and polysaccharides, that are present in lesion tissue, thus preventing these inhibitors from adversely affecting the PCR assay of the present invention.

Many leaves inoculated with the *P. medicaginis*-like or *D. bryoniae*-New York variant spores did not yield any visible lesions, although the respective primer sets detected the presence of the fungi. It is possible that either infection was latent or that the primers were capable of detecting residual spores present at the points of inoculation. These results indicate the present invention may be useful to help reduce the incidence of gummy stem blight, by permitting the testing of geenhouse transplants for latent and early infections.

Although preferred embodiments of the invention have been described using specific terms, devices, concentrations, and methods, such description is for illustrative purposes only. The words used are words of description rather than of limitation. It is to be understood that changes and variations may be made without departing from the spirit or the scope of the following claims.

What is claimed is:

1. A method for objectively distinguishing the presence of non-pathogenic fungi from a *Didymella bryoniae* fungal infection in a whole plant, plant extract, or plant seed by using cycles of a polymerase chain reaction, said method comprising the steps of:

(a) removing a sample of leaf, stem, or seed from a plant to be tested;

(b) extracting genomic DNA from said sample to use as a DNA template;

(c) replicating a desired region in the DNA template by binding a specific oligonucleotide primer set comprising SEQ ID No. 13 and SEQ ID NO. 14 to said DNA template in a complimentary fashion, said primer set designed to give rise to a desired PCR product having a size different from the size of a product produced from amplifying undesired genomic DNA;

(d) amplifying said DNA template by conducting the polymerase chain reaction from about 25 cycles to about 35 cycles to produce a PCR product; and, (e) examining said PCR product to identify *Didymella bryoniae* or nonpathogenic fungal infection present in said sample.

2. The method as in claim 1, wherein said PCR product is examined by visualizing said PCR product in an ethidium bromide stained-agarose gel and comparing said PCR product to a standard DNA ladder to determine size of said PCR product.

3. The method of claim 1, wherein the size of said desired PCR product is approximately 650 base pairs in length.

4. The method of claim 1, wherein the size of said desired PCR product is approximately 450 base pairs in length.

5. The method of claim 1, wherein said non-pathogenic fungi are distinguished from a *Didymella bryoniae* infection by examining said PCR product by colorimetric visualization, said method comprising the steps of:

(a) producing said PCR product containing a biotin moiety at a 5' end of a forward strand and a fluorescein moiety at a 5' end of a reverse strand of said PCR product;

(b) attaching said PCR product to a well of a microtiter plate, said well coated with avidin such that said PCR product is bound chemically via said biotin moiety, and subsequently washing away excess or unbound PCR product;

(c) attaching an enzyme to said PCR product via said fluorescein moiety, and subsequently washing away excess or unbound enzyme;

(d) adding a color substrate to said well, whereby said color substrate reacts with said enzyme to produce a colored product; and (e) measuring the intensity of said colored product using an ELISA reader.

6. The method of claim 1, wherein said PCR product is identified by hybridization of said PCR product with a radioactively-labeled oligonucleotide probe having a sequence unique to said non-pathogenic fungi.

7. The method in claim 1, wherein said polymerase chain reaction is run for 30 cycles.

8. A method for objectively distinguishing the presence of non-pathogenic fungi from a *Didymella bryoniae* fungal infection in a whole plant, plant extract, or plant seed by using cycles of a polymerase chain reaction, said method comprising the steps of:

(a) removing a sample of leaf, stem, or seed from a plant to be tested;

(b) extracting genomic DNA from said sample to use as a DNA template;

(c) replicating a desired region in the DNA template by binding a specific oligonucleotide primer set comprising SEQ ID NO. 15 and SEQ ID NO. 16 to said DNA template in a complimentary fashion, said primer set designed to give rise to a desired PCR product having a size different from the size of a product produced from amplifying undesired genomic DNA;

(d) amplifying said DNA template by conducting the polymerase chain reaction from about 25 cycles to about 35 cycles to produce a PCR product; and, (e) examining said PCR product to identify a *Didymella bryoniae* or non-pathogenic fungal infection present in said sample.

9. The method of claim 8, wherein said PCR product is examined by visualizing said PCR product in an ethidium bromide stained-agarose gel and comparing said PCR product to a standard DNA ladder to determine size of said PCR product.

10. The method of claim 8, wherein the size of said desired PCR product is approximately 650 base pairs in length.

11. The method of claim 8, wherein the size of said desired PCR product is approximately 450 base pairs in length.

12. The method of claim 8, wherein said non-pathogenic fungi are distinguished from a *Didymella bryoniae* infection by examining said PCR product by calorimetric visualization, said method comprising the steps of:

(a) producing said PCR product containing a biotin moiety at the 5' end of a forward strand and a fluorescein moiety at a 5' end of a reverse strand of said PCR product;

(b) attaching said PCR product to a well of a microtiter plate, said well coated with avidin such that said PCR product is bound chemically via said biotin moiety, and subsequently washing away excess or unbound PCR product;

(c) attaching an enzyme to said PCR product via said fluorescein moiety, and subsequently washing away excess or unbound enzyme;

(d) adding a color substrate to said well, whereby said color substrate reacts with said enzyme to produce a colored product; and (e) measuring the intensity of said colored product using an ELISA reader.

13. The method of claim 1, wherein said PCR product is identified by hybridization of said PCR product with a radioactively-labeled oligonucleotide probe having a sequence unique to said non-pathogenic fungi.

14. The method of claim 8, wherein said polymerase chain reaction is run for 30 cycles.

* * * * *

```
                              SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
         (A) LENGTH: 10 base pairs
         (B) TYPE: Nucleic Acid
         (C) STRANDEDNESS: Single
         (D) TOPOLOGY: Linear (ii) MOLECULE TYPE: Other Nucleic Acid
         (A) DESCRIPTION: Oligonucleotide Primer (iii) HYPOTHETICAL: No (iv) ANTI-SENSE: No (vi) ORIGINAL SOURCE: Operon Technologies (Alemeda, CA)

(vii) IMMEDIATE SOURCE: Operon Technologies (viii) POSITION IN GENOME: Not Applicable
         (C) UNITS:

(ix) FEATURE:
         (D) OTHER INFORMATION: Commercially Available Primer (x) PUBLICATION INFORMATION:
         (A) AUTHORS: Keinath, Anthony P., Farnham, M. W., and Zitter,
             T. A.
         (B) TITLE:     Morphological, Pathological, and Genetic
             Differentiation of Didymella bryoniae and Phoma Spp.
             Isolated From Cucurbits
         (C) JOURNAL: Phytopathology
         (D) VOLUME:    85
         (E) ISSUE: 3
         (F) PAGES:
         (G) DATE: 1995

(xi) SEQUENCE DESCRIPTION:   SEQ ID NO: 1:

GGGCCACTCA                                                                10

(2) INFORMATION FOR SEQ ID NO: 2:

(i) SEQUENCE CHARACTERISTICS:
         (A) LENGTH: 10 Pairs
         (B) TYPE: Nucleic Acid
         (C) STRANDEDNESS: Single
         (D) TOPOLOGY: Linear (ii) MOLECULE TYPE: Other Nucleic Acid
         (A) DESCRIPTION: Oligonucleotide Primer (iii) HYPOTHETICAL: No (iv) ANTI-SENSE: No (vi) ORIGINAL SOURCE: Operon Technologies (Alemeda, CA)

(vii) IMMEDIATE SOURCE: Operon Technologies
```

```
     (viii) POSITION IN GENOME: Not Applicable
           (C) UNITS:

(ix) FEATURE:
           (D) OTHER INFORMATION: Commercially Available Primer (x) PUBLICATION INFORMATION:
           (A) AUTHORS: Keinath, Anthony P., Farnham, M. W., and Zitter,
               T. A.
           (B) TITLE:    Morphological, Pathological, and Genetic
               Differentiation of Didymella bryoniae and Phoma Spp.
               Isolated From Cucurbits
           (C) JOURNAL: Phytopathology
           (D) VOLUME:    85
           (E) ISSUE: 3
           (F) PAGES:
           (G) DATE: 1995

(xi) SEQUENCE DESCRIPTION:  SEQ ID NO: 2:

GGCAGGCTGT                                                                     10

(2) INFORMATION FOR SEQ ID NO:3:

(i) SEQUENCE CHARACTERISTICS:
           (A) LENGTH: 10 Pairs
           (B) TYPE: Nucleic Acid
           (C) STRANDEDNESS: Single
           (D) TOPOLOGY: Linear (ii) MOLECULE TYPE: Other Nucleic Acid
           (A) DESCRIPTION: Oligonucleotide Primer (iii) HYPOTHETICAL: No (iv) ANTI-SENSE: No (vi) ORIGINAL SOURCE: Operon Technologies (Alemeda, CA)

(vii) IMMEDIATE SOURCE: Operon Technologies (viii) POSITION IN GENOME: Not Applicable
           (C) UNITS:

(ix) FEATURE:
           (D) OTHER INFORMATION: Commercially Available Primer (x) PUBLICATION INFORMATION: Not Applicable (xi) SEQUENCE DESCRIPTION:  SEQ ID NO: 3:

GGGTGTGTAG                                                                     10

(2) INFORMATION FOR SEQ ID NO:4:

(i) SEQUENCE CHARACTERISTICS:
           (A) LENGTH: 10 Pairs
           (B) TYPE: Nucleic Acid
           (C) STRANDEDNESS: Single
           (D) TOPOLOGY: Linear (ii) MOLECULE TYPE: Other Nucleic Acid
           (A) DESCRIPTION: Oligonucleotide Primer (iii) HYPOTHETICAL: No (iv) ANTI-SENSE: No (vi) ORIGINAL SOURCE: Operon Technologies (Alemeda, CA)

(vii) IMMEDIATE SOURCE:  Operon Technologies (viii) POSITION IN GENOME: Not Applicable
           (C) UNITS:

(ix) FEATURE:
           (D) OTHER INFORMATION: Commercially Available Primer
```

(x) PUBLICATION INFORMATION: Not Applicable (xi) SEQUENCE DESCRIPTION:  SEQ ID NO: 4:

AGGACTGCCA                                                                      10

(2) INFORMATION FOR SEQ ID NO:5:

(i) SEQUENCE CHARACTERISTICS:
             (A) LENGTH: 10 Pairs
             (B) TYPE: Nucleic Acid
             (C) STRANDEDNESS: Single
             (D) TOPOLOGY: Linear (ii) MOLECULE TYPE: Other Nucleic Acid
             (A) DESCRIPTION: Oligonucleotide Primer (iii) HYPOTHETICAL: No (iv) ANTI-SENSE: No (vi) ORIGINAL SOURCE: Operon Technologies (Alemeda, CA)

(vii) IMMEDIATE SOURCE:  Operon Technologies (viii) POSITION IN GENOME: Not Applicable
             (C) UNITS:

(ix) FEATURE:
             (D) OTHER INFORMATION: Commercially Available Primer (x) PUBLICATION INFORMATION: Not Applicable (xi) SEQUENCE DESCRIPTION:  SEQ ID NO: 5:

AATGCCGCAG                                                                      10

(2) INFORMATION FOR SEQ ID NO:6:

(i) SEQUENCE CHARACTERISTICS:
             (A) LENGTH: 10 Pairs
             (B) TYPE: Nucleic Acid
             (C) STRANDEDNESS: Single
             (D) TOPOLOGY: Linear (ii) MOLECULE TYPE: Other Nucleic Acid
             (A) DESCRIPTION: Oligonucleotide Primer (iii) HYPOTHETICAL: No (iv) ANTI-SENSE: No (vi) ORIGINAL SOURCE: Operon Technologies (Alemeda, CA)

(vii) IMMEDIATE SOURCE: Operon Technologies (viii) POSITION IN GENOME: Not Applicable
             (C) UNITS:

(ix) FEATURE:
             (D) OTHER INFORMATION: Commercially Available Primer (x) PUBLICATION INFORMATION: Not Applicable (xi) SEQUENCE DESCRIPTION:  SEQ ID NO: 6:

GATGCCAGAC                                                                      10

(2) INFORMATION FOR SEQ ID NO:7:

(i) SEQUENCE CHARACTERISTICS:
             (A) LENGTH: 10 Pairs
             (B) TYPE: Nucleic Acid
             (C) STRANDEDNESS: Single
             (D) TOPOLOGY: Linear

```
    (ii) MOLECULE TYPE: Other Nucleic Acid
         (A) DESCRIPTION: Oligonucleotide Primer (iii) HYPOTHETICAL: No (iv) ANTI-SENSE: No (vi) ORIGINAL SOURCE: Operon Technologies (Alemeda, CA)

(vii) IMMEDIATE SOURCE: Operon Technologies (viii) POSITION IN GENOME: Not Applicable
         (C) UNITS:

(ix) FEATURE:
         (D) OTHER INFORMATION: Commercially Available Primer (x) PUBLICATION INFORMATION: Not Applicable (xi) SEQUENCE DESCRIPTION:   SEQ ID NO: 7:

CATTCGAGCC                                                              10

(2) INFORMATION FOR SEQ ID NO:8:

(i) SEQUENCE CHARACTERISTICS:
         (A) LENGTH: 10 Pairs
         (B) TYPE: Nucleic Acid
         (C) STRANDEDNESS: Single
         (D) TOPOLOGY: Linear (ii) MOLECULE TYPE: Other Nucleic Acid
         (A) DESCRIPTION: Oligonucleotide Primer (iii) HYPOTHETICAL: No (iv) ANTI-SENSE: No (vi) ORIGINAL SOURCE: Operon Technologies (Alemeda, CA)

(vii) IMMEDIATE SOURCE: Operon Technologies (viii) POSITION IN GENOME: Not Applicable
         (C) UNITS:

(ix) FEATURE:
         (D) OTHER INFORMATION: Commercially Available Primer (x) PUBLICATION INFORMATION: Not Applicable (xi) SEQUENCE DESCRIPTION:   SEQ ID NO: 8:

CCGCCCAAAC                                                              10

(2) INFORMATION FOR SEQ ID NO:9:

(i) SEQUENCE CHARACTERISTICS:
         (A) LENGTH: 10 Pairs
         (B) TYPE: Nucleic Acid
         (C) STRANDEDNESS: Single
         (D) TOPOLOGY: Linear (ii) MOLECULE TYPE: Other Nucleic Acid
         (A) DESCRIPTION: Oligonucleotide Primer (iii) HYPOTHETICAL: No (iv) ANTI-SENSE: No (vi) ORIGINAL SOURCE: Operon Technologies (Alemeda, CA)

(vii) IMMEDIATE SOURCE: Operon Technologies (viii) POSITION IN GENOME: Not Applicable
         (C) UNITS:
```

```
    (ix) FEATURE:
         (D) OTHER INFORMATION: Commercially Available Primer (x) PUBLICATION INFORMATION: Not Applicable (xi) SEQUENCE DESCRIPTION:  SEQ ID NO: 9:

GAACACTGGG                                                              10

(2) INFORMATION FOR SEQ ID NO:10:

(i) SEQUENCE CHARACTERISTICS:
         (A) LENGTH: 10 Pairs
         (B) TYPE: Nucleic Acid
         (C) STRANDEDNESS: Single
         (D) TOPOLOGY: Linear (ii) MOLECULE TYPE: Other Nucleic Acid
         (A) DESCRIPTION: Oligonucleotide Primer (iii) HYPOTHETICAL: No (iv) ANTI-SENSE: No (vi) ORIGINAL SOURCE: Operon Technologies (Alemeda, CA)

(vii) IMMEDIATE SOURCE: Operon Technologies (viii) POSITION IN GENOME: Not Applicable
         (C) UNITS:

(ix) FEATURE:
         (D) OTHER INFORMATION: Commercially Available Primer (x) PUBLICATION INFORMATION: Not Applicable (xi) SEQUENCE DESCRIPTION:  SEQ ID NO: 10:

CCCTACCGAC                                                              10

(2) INFORMATION FOR SEQ ID NO: 11:

(i) SEQUENCE CHARACTERISTICS:
         (A) LENGTH: 21 base pairs
         (B) TYPE: Nucleic Acid
         (C) STRANDEDNESS: Single
         (D) TOPOLOGY: Linear (ii) MOLECULE TYPE: Other Nucleic Acid
         (A) DESCRIPTION: Oligonucleotide Primer (iii) HYPOTHETICAL: No (iv) ANTI-SENSE: No (vi) ORIGINAL SOURCE: Design Based on the Sequence Information from
             RAPD Fragments Generated From Didymella bryoniae (DB)

(vii) IMMEDIATE SOURCE: Integrated DNA Technologies (Coralville, IA)

(viii) POSITION IN GENOME: Not Applicable
         (C) UNITS:

(ix) FEATURE:
         (D) OTHER INFORMATION: Forward Primer (xi) SEQUENCE DESCRIPTION:  SEQ ID NO: 11:

TGTCGTTGAC ATCATTCCAG C                                                 21

(2) INFORMATION FOR SEQ ID NO: 12:

(i) SEQUENCE CHARACTERISTICS:
         (A) LENGTH: 21 base pairs
         (B) TYPE: Nucleic Acid
         (C) STRANDEDNESS: Single
```

(D) TOPOLOGY: Linear (ii) MOLECULE TYPE: Other Nucleic Acid
        (A) DESCRIPTION: Oligonucleotide Primer (iii) HYPOTHETICAL: No (iv) ANTI-SENSE: Yes (vi) ORIGINAL SOURCE: Design Based on the Sequence Information from
            RAPD Fragments Generated From Didymella bryoniae (DB)

(vii) IMMEDIATE SOURCE: Integrated DNA Technologies (Coralville, IA)

(viii) POSITION IN GENOME: Not Applicable
        (C) UNITS:

(ix) FEATURE:
(D) OTHER INFORMATION: Reverse Primer (xi) SEQUENCE DESCRIPTION: SEQ ID NO: 12:

ACCACTCTGC TTAGTATCTG C 21

(2) INFORMATION FOR SEQ ID NO: 13:

(i) SEQUENCE CHARACTERISTICS:
(A) LENGTH: 21 base pairs
(B) TYPE: Nucleic Acid
(C) STRANDEDNESS: Single
(D) TOPOLOGY: Linear (ii) MOLECULE TYPE: Other Nucleic Acid
(A) DESCRIPTION: Oligonucleotide Primer (iii) HYPOTHETICAL: No (iv) ANTI-SENSE: No (vi) ORIGINAL SOURCE: Design Based on the Sequence Information from RAPD Fragments Generated From Phoma medicaginis-like (PM) isolates (vii) IMMEDIATE SOURCE: Integrated DNA Technologies (Coralville, IA)

(viii) POSITION IN GENOME: Not Applicable
(C) UNITS:

(ix) FEATURE:
(D) OTHER INFORMATION: Forward Primer (xi) SEQUENCE DESCRIPTION: SEQ ID NO: 13:

GTCAGAGTTC AGAATGCTTC G 21

(2) INFORMATION FOR SEQ ID NO: 14:

(i) SEQUENCE CHARACTERISTICS:
(A) LENGTH: 21 base pairs
(B) TYPE: Nucleic Acid
(C) STRANDEDNESS: Single
(D) TOPOLOGY: Linear (ii) MOLECULE TYPE: Other Nucleic Acid
(A) DESCRIPTION: Oligonucleotide Primer (iii) HYPOTHETICAL: No (iv) ANTI-SENSE: Yes (vi) ORIGINAL SOURCE: Design Based on the Sequence Information from RAPD Fragments Generated From Phoma medicaginis-like (PM) isolates (vii) IMMEDIATE SOURCE: Integrated DNA Technologies (Coralville, IA)

(viii) POSITION IN GENOME: Not Applicable

```
            (C) UNITS:

(ix) FEATURE:
         (D) OTHER INFORMATION: Reverse Primer (xi) SEQUENCE DESCRIPTION:  SEQ ID NO: 14:

ACGGATGAAT AACACGGAAG A                                                      21

(2) INFORMATION FOR SEQ ID NO: 15:

(i) SEQUENCE CHARACTERISTICS:
         (A) LENGTH: 21 base pairs
         (B) TYPE: Nucleic Acid
         (C) STRANDEDNESS: Single
         (D) TOPOLOGY: Linear (ii) MOLECULE TYPE: Other Nucleic Acid
         (A) DESCRIPTION: Oligonucleotide Primer (iii) HYPOTHETICAL: No (iv) ANTI-SENSE: No (vi) ORIGINAL SOURCE: Design Based on the Sequence Information from
             RAPD Fragments Generated From Didymella bryoniae-New York
             variant (NY) isolates (vii) IMMEDIATE SOURCE: Integrated DNA Technologies (Coralville, IA)

(viii) POSITION IN GENOME: Not Applicable
         (C) UNITS:

(ix) FEATURE:
         (D) OTHER INFORMATION: Forward Primer (xi) SEQUENCE DESCRIPTION:  SEQ ID NO: 15:

GCTAAGCCTT AATCTAGCTG C                                                      21

(2) INFORMATION FOR SEQ ID NO: 16:

(i) SEQUENCE CHARACTERISTICS:
         (A) LENGTH: 21 base pairs
         (B) TYPE: Nucleic Acid
         (C) STRANDEDNESS: Single
         (D) TOPOLOGY: Linear (ii) MOLECULE TYPE: Other Nucleic Acid
         (A) DESCRIPTION: Oligonucleotide Primer (iii) HYPOTHETICAL: No (iv) ANTI-SENSE: Yes (vi) ORIGINAL SOURCE: Design Based on the Sequence Information from
             RAPD Fragments Generated From Didymella bryoniae-New York
             variant (NY) isolates (vii) IMMEDIATE SOURCE: Integrated DNA Technologies (Coralville, IA)

(viii) POSITION IN GENOME: Not Applicable
         (C) UNITS:

(ix) FEATURE:
         (D) OTHER INFORMATION: Reverse Primer (xi) SEQUENCE DESCRIPTION:  SEQ ID NO: 16:

GAGAGTAAGC TAACCTAAAG G                                                      21
```